(12) United States Patent
Xu

(10) Patent No.: US 10,039,910 B2
(45) Date of Patent: Aug. 7, 2018

(54) PLUMBER-LIKE MASS TRANSPORT DEVICE FOR DERMAL AND TRANSDERMAL DELIVERY OF A LIQUID OR SOLID COMPOSITION

(71) Applicant: NANOMED SKINCARE, INC., Cupertino, CA (US)

(72) Inventor: Bai Xu, Cupertino, CA (US)

(73) Assignee: NANOMED SKINCARE, INC., Cupertino, CA (US)

( * ) Notice: Subject to any disclaimer, the term of this patent is extended or adjusted under 35 U.S.C. 154(b) by 538 days.

(21) Appl. No.: 14/668,648

(22) Filed: Mar. 25, 2015

(65) Prior Publication Data
US 2015/0273195 A1 Oct. 1, 2015

Related U.S. Application Data

(60) Provisional application No. 61/970,589, filed on Mar. 26, 2014.

(51) Int. Cl.
*A61M 35/00* (2006.01)
*A61M 5/315* (2006.01)

(52) U.S. Cl.
CPC ........ *A61M 35/003* (2013.01); *A61M 5/3159* (2013.01); *A61M 5/31576* (2013.01)

(58) Field of Classification Search
CPC ............ A61M 5/31576; A61M 5/3159; A61M 35/003; A61M 37/0015
See application file for complete search history.

(56) References Cited

U.S. PATENT DOCUMENTS

| | | | | |
|---|---|---|---|---|
| 4,708,716 A | * | 11/1987 | Sibalis | A61M 37/00 424/449 |
| 2002/0077584 A1 | * | 6/2002 | Lin | A61B 5/14532 604/21 |
| 2005/0098583 A1 | * | 5/2005 | Mbonyumuhire | B05B 11/0016 222/321.7 |
| 2014/0044805 A1 | * | 2/2014 | Kiss | A61M 37/00 424/700 |
| 2014/0336536 A1 | * | 11/2014 | Brancazio | A61B 5/1411 600/583 |
| 2015/0258319 A1 | * | 9/2015 | Simmers | A61M 37/0015 604/506 |

* cited by examiner

*Primary Examiner* — Benjamin Klein
(74) *Attorney, Agent, or Firm* — Nath, Goldberg & Meyer; Joshua B. Goldberg; James Lafave

(57) ABSTRACT

A plunger-like mass transporting device and method for controllable transportation of a selected dosage of a solid or liquid composition having a body with a rigid enclosure, and a head, where the head is configured to attach to the body, the head having a stem and a housing. Further, the stem having a first end, the first end having an attachment means to attach to the rigid enclosure containing the body; and a second end, the second end having an attachment means to attach to the housing, and an applicator; wherein a flexible means is disposed on the stem, for providing an up position and a down position during an axial movement of the stem back and forth through the housing, wherein the housing contains the solid or liquid composition.

15 Claims, 3 Drawing Sheets

Figure 1:
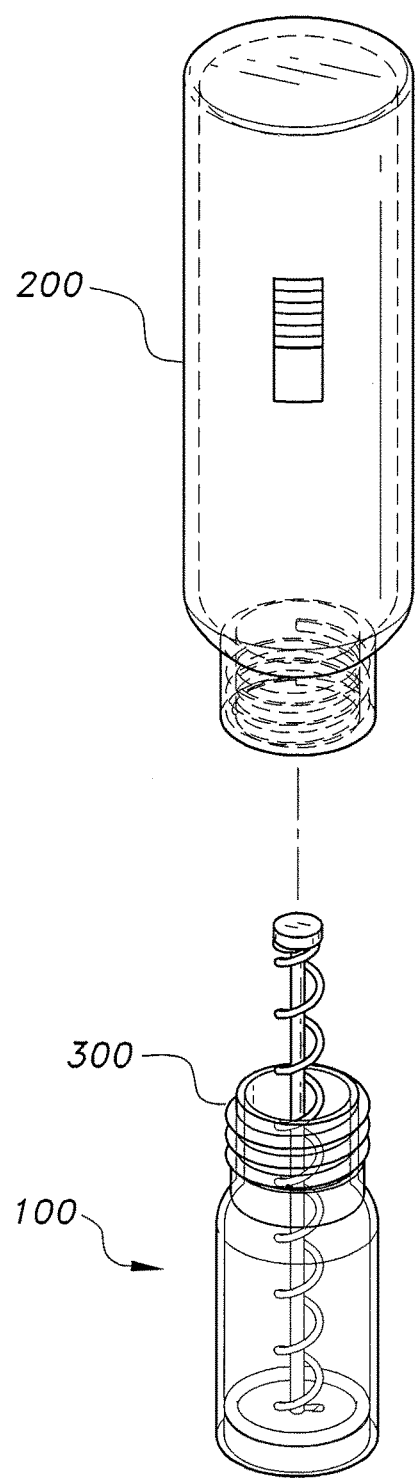

PLUMBER-LIKE MASS TRANSPORT DEVICE FOR DERMAL AND TRANSDERMAL DELIVERY OF A LIQUID OR SOLID COMPOSITION

TECHNICAL FIELD

The present application relates to a plunger-like mass transportation device for dermal and transdermal delivery of liquid or solid compositions, and methods of using the same.

BACKGROUND

Drugs are commonly administered in solid form through pills or capsules that can be orally taken. However, many biological drugs cannot be administered this way because of degradation in the gastrointestinal tract and quick elimination by the liver. Another common technique for administration of drugs in liquid form is through injection using a metal hypodermic needle that can cause significant pain and discomfort to patients. For example, U.S. Pat. No. 5,279,585 discloses an injection device is provided for injecting fluids such as insulin within body tissue. The device includes a housing, a piston rod movably mounted within the housing, and a dose setting mechanism for controlling the movement of the piston rod with respect to a fluid-containing cartridge removably positioned within the housing.

Similarly, a number of physical and chemical techniques including electroporation, laser ablation, ultrasound, thermal, iontophoresis, and chemical enhancers have been explored to develop painless transdermal drug delivery techniques. It was found that its very difficult for the molecules with a molecular weight higher than 500 or diameter larger than 1 nm to penetrate normal human skin. Further studies showed that the key barrier for transdermal delivery of substances is the stratum corneum layer, the outer layer of skin, that is about 4-30 micron thick. Invasive methods to overcome this skin barrier have been used in practice, such as intradermal (ID), intramuscular (IM), or subcutaneous (SC) injection using standard hypodermic needles and syringes. These methods cause pain and require a skilled professional. In addition, they may cause needle injuries. Similarly, current methods of extracting biologic fluids such as blood from patients suffer from the same disadvantages.

In order to improve the skin permeability of the therapeutic agents and other active ingredients, microneedles have been recently developed to disrupt the stratum corneum and facilitate the delivery of the active agents and ingredients to the epidermis. These active substances can then diffuse through the rest of the epidermis to the dermis and be absorbed by blood vessels and lymphatics there. The substance absorbed can then get into the circulation system. Thus, both topical and systemic-level delivery of drugs is possible. Since there are no nerves and blood vessels in the stratum corneum and epidermis, this is a minimally invasive, painless and blood-free method of drug delivery. An additional advantage of this method, when engineered for topical delivery of vaccines, can lead to an enhanced inoculation effect because the epidermis is rich in antigen presenting cells and is a desired target for vaccine delivery.

SUMMARY

The present application is directed towards a plunger-like mass transporting device for controllable transportation of a selected dosage of a solid or liquid composition comprising a body having a rigid enclosure, and ahead, the head configured to attach to the body, the head having a stem and a housing. Further, the stem having a first end, the first end having an attachment means to attach to the rigid enclosure containing the body; and a second end, the second end having an attachment means to attach to the housing, and an applicator; wherein a flexible means is disposed on the stem, for providing an up position and a down position during an axial movement of the stem back and forth through the housing, wherein the housing contains the solid or liquid composition.

The present application is also directed towards a method of using the plunger-like device for delivery of a liquid or solid composition to skin of a patient. The method comprises the steps of determining an appropriate delivery site on a patient in need of the composition; placing the device so that the applicator is proximate to the delivery site; and activating the device to deliver the composition. The method can optionally be used in creating self-healing nanopores on the skin of the patient for transdermal delivery of the administered composition.

BRIEF DESCRIPTION OF THE DRAWINGS

FIG. 1 depicts the plunger-like mass transportation device with the body and the head.

FIG. 2 depicts a head portion of the device.

FIG. 3 depicts a head portion of the device, where the flexible means is in a compressed state and the applicator is attached to nanochips.

DETAILED DESCRIPTION

All technical and scientific terms used herein have the same meanings as commonly understood by someone ordinarily skilled in the art to which this subject matter belongs. The following definitions are provided for the purpose of understanding the present subject matter and for constructing the appended patent claims.

The term "a" or "an" as used herein includes the singular and the plural, unless specifically stated otherwise. Therefore, the term "a," "an" or "at least one" can be used interchangeably in this application.

Throughout the application, descriptions of various embodiments use the term "comprising"; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used herein, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

As used herein, "nanochips" are structures used to pierce through the outer skin barrier layer, and deliver the liquid or solid composition to the epidermis or even deeper. The nanochips can also be shaped as microneedles, microknives, or microblades.

As used herein, "attachment means" encompasses a mechanism for attaching the stem to the body of the plunger-like mass transportation device. Examples of attachment means include, but are not limited to, screwing threads, flexible attachment membranes and adhesives.

As used herein, "flexible means" encompasses any object that is capable of providing elasticity to the stem in moving the stem back and forth. Examples of flexible means include, but are not limited to, springs and elastic bands.

As used herein, "skin" of a patient also includes mucosal layers of a patient's body, in addition to the stratum corneum, dermis, and/or epidermis of the patient.

Other terms as used herein are meant to be defined by their well-known meaning in the art.

FIG. 1 depicts a plunger-like mass transportation device 10. The device 10 comprises a head 100 and a body 200. The head has an attachment means 300 to attach the head 100 to the body 200 of the device 10. In one embodiment, the attachment means 300 are threads on the head 100 of the device 10, so that the head 100 screws onto the body 200 of the device 10, or vice-versa. In other embodiments, the attachment means 300 is an adhesive, to temporarily or permanently fix the head 100 to the body 200 of the device 10. Further, in another embodiment, the attachment means 300 clicks onto the body 200 of the device 10. The head 100 is configured to attach to the body 200, such that the head 100 is easily and readily detachable or removable from the body 200. Additionally, in some embodiments, the head 100 is disposable.

The body 200 of the device 10 is shaped such that it can be easily held in the hand. The body 200 has a rigid enclosure with a first end and a second end. The first end of the body is configured in such a way that it receives the head 100 of the device 10. In one embodiment, the body 200 of the device 10 comprises a motor that enables the head 100 to perform an up-down movement when the device 10 is activated. Other means for performing this up-down movement are further contemplated herein.

In some embodiments, the body 200 of the device 10 comprises: (a) a second housing having a plurality of walls defining an interior space, the interior space having an upper opening permitting selective access to the interior space of the second housing, a cover member being removably couplable to the second housing such that the cover is for closing the upper opening of the interior space of the second housing; and (b) a head 100 connected to a first end of the body 200 removably insertable into the interior space of the second housing, where the device 10 being adapted for aiding a patient to treat skin.

In some embodiments, the body 200 of the device 10 can further comprises a motor assembly being positioned in a base portion, a top portion having a drive assembly being positioned in the top portion, the drive assembly being operationally coupled to a base portion, the base portion outwardly extending from an upper end of the head portion, the motor assembly being operationally coupled to the drive assembly such that the motor assembly is for actuating the drive assembly, the drive assembly being for oscillating the base portion when the drive assembly is actuated by the motor assembly.

In some embodiments, the body 200 of the device 10 described above can further comprise a motor assembly having a motor, the motor having a shaft extending from the motor, the motor being for actuating the shaft, the shaft being for operationally coupling to the drive assembly of the base and head portions such that actuation of the shaft actuates the drive assembly, a power source being operationally coupled to the motor such that the power supply is for providing power to the motor.

In some embodiments, the body 200 of the device 10 described above can include a heavy eccentric mass designed to produce vibration upon actuation of the motor, wherein the motor is actuated to bring the base and head portions into vibration so that skin treatment is practiced through the aid of the vibration, the microneedle application method comprising the steps of: predetermining respective weights of the electric body 200 of the device 10 and the heavy eccentric mass as well as an eccentric location of the center of gravity of the heavy eccentric mass; establishing an output of the motor at about 1000-15000 rpm in accordance with the predetermined conditions; producing a vibration of about 1000-15000 rpm by actuating the motor; conducting the vibration to increase a pressing force acting along an axial direction of the body 200 of the device 10 by the use of a minute circular ring connecting to the handle part and pressing against skin area need treatment.

In some embodiments, the body 200 of the device 10 described above can further include a motor assembly having a switch, the switch being operationally coupled between the power supply and the motor, the switch being for controlling power from the power supply to the motor. In other embodiments, the device can be operated manually.

In a preferred embodiment, the body 200 has a flexible means that allows a head 100 connected to the first end of the body 200 to perform an up-down axial movement or back and forth movement. In one embodiment, the body 200 of the device 10 has an activation button or an on-off switch. In some embodiments, the body 200 of the device 10 is operated with batteries. In other embodiments, the body 200 of the device 10 is operated on electricity.

Figure 2:
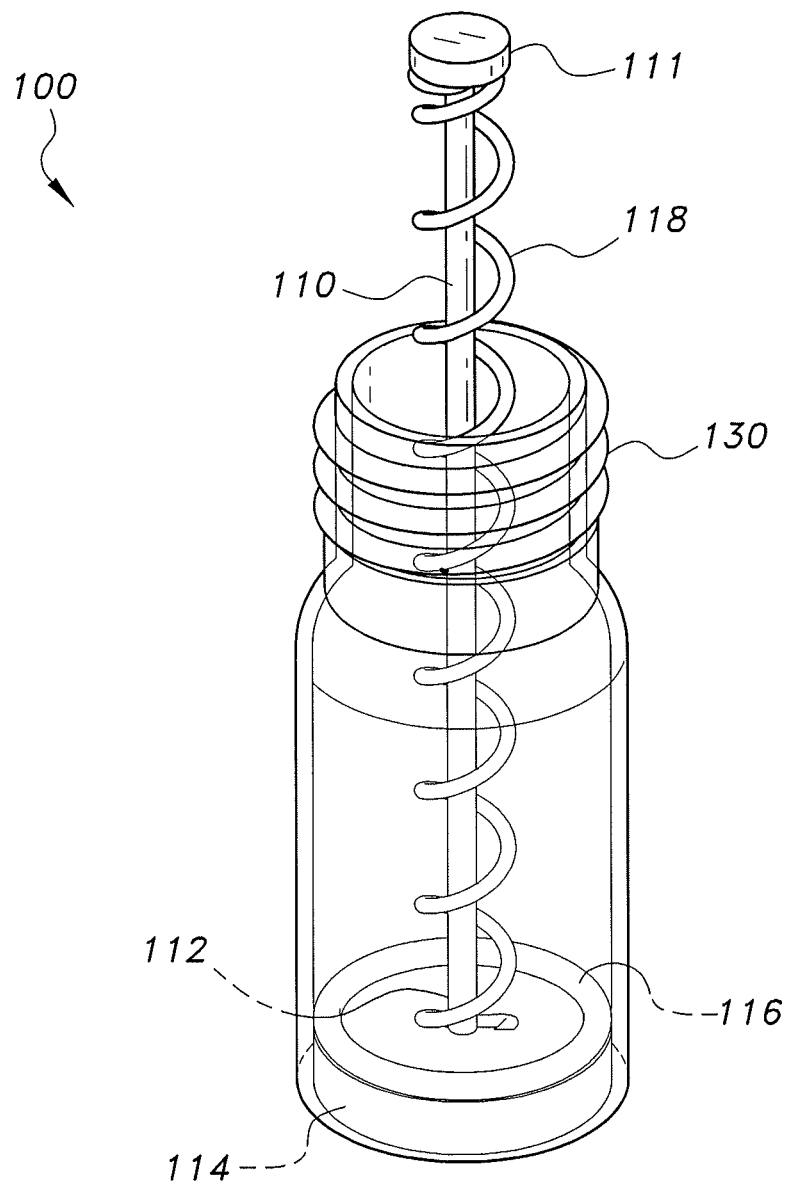

FIG. 2 of the present application depicts a head 100 of a plunger-like mass transportation device. The head comprises a stem 110 and a housing 120. In a preferred embodiment, the head 100 of the device 10 is capable of holding between 0.001-30 ml of the liquid or solid composition. In another embodiment, the liquid or solid composition is storage stable in the head 100 for about one month to about two years.

The stem 110 further comprises a first end 111, and a second end 112. The first end 111 has an attachment means to attach to a body 200 of the plunger-like mass transportation device 10. The first end 111 of the stem 110 is configured in a way that is complimentary to the first end of the body 200, such that the first end of the body 200 and the first end 111 of the stem 110 attach to each other. In some embodiments, a membrane is provided around the first end of the stem 111 and a part of the housing 120 proximate to the first end of the stem 111 to enable proper attachment between the head 100 and the body 200 of the device 10.

In one embodiment, the stem has a travel distance of greater than 0.1 mm. In another embodiment, the frequency of the axial movement of the stem is greater than 1 Hz.

The second end 112 of the stem 110 is located at a distance from the first end 111 of the stem 110. The second end 112 of the stem 110 has an applicator 114 for delivery of the liquid or solid composition onto the skin of the patient. In one embodiment, the stem 110 comprises a reservoir within it that holds the liquid or solid composition. In some embodiments, the applicator 114 is impervious. In other embodiments, the applicator 114 is made of silicone.

In a preferred embodiment, the applicator 114 is placed proximate to a sealant 116. In one embodiment, the sealant 116 is placed around the applicator 114. In another embodiment, the sealant 116 is placed above the applicator 116. In one embodiment, the sealant 116 is selected from a group consisting of a membrane and a ring. In a preferred embodiment, the ring is made of rubber or an elastic material. In other embodiments, the applicator 114 is placed in such a way that it contacts the patient's skin for delivery of the composition.

Figure 3:
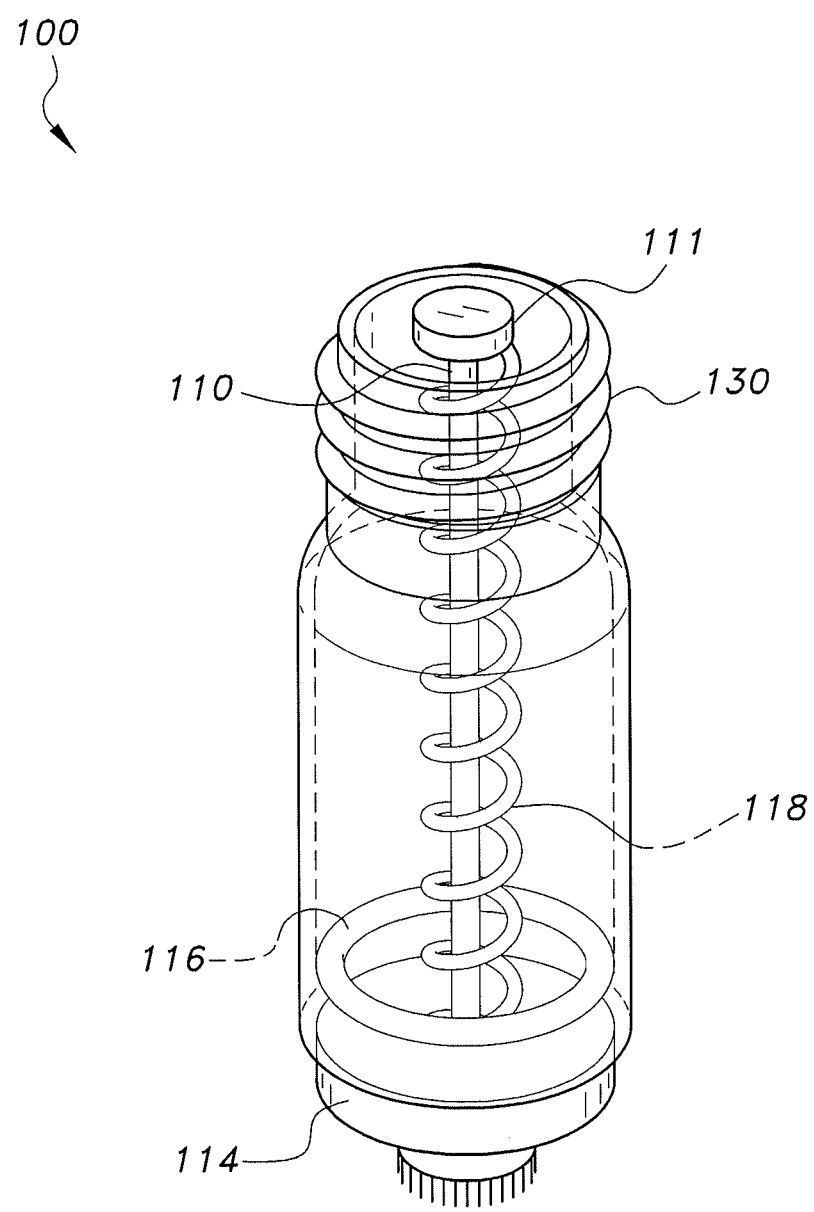

In one embodiment, nanochips 140 are attached to the exterior of the applicator 114, as shown in FIG. 3 of the present application, such that the nanochips 140 create self-healing nanopores at the point of contact on the skin of the patient. This is particularly useful for transdermal delivery of liquid or solid compositions. The diameter of a single microneedle is in the range of 30-300 microns with a sharp tip of less than 10 microns to cause little discomfort to the patients while maintaining mechanical integrity. In one embodiment, the needle tip is less than 2 microns and the height of the needle shaft is about 100 microns. The aspect ratio can be 5:1, 10:1, 15:1, 20:1, 50:1 or higher in some embodiments.

In some embodiments, the present application provides a system for topical or systemic delivery of a liquid or solid composition to skin of the patient. The system comprises: (1) a plunger-like mass transportation device 10 comprising an array of microstructures on an applicator 114 of a head 110 for applying the device 10 to an area of skin of a patient to generate a prepared area of skin comprising a plurality of nanopores or nanochannels in stratum corneum of the prepared area of skin, and (2) a delivery mechanism for causing the liquid or solid composition to be delivered to the mammal through the nanopores or nanochannels in the stratum corneum of the prepared area of skin. In some embodiments, the device 10 can comprise nanoscale tips and microscale body that can have an aspect ratio of about 5:1, 10:1, 15:1, 20:1 or higher.

The device 10 described herein can be used for effective transdermal delivery of liquid or solidcomposition. The device 10 can have a head 100 having a microneedle array which comprises a plurality of nanochips 140 formed of a metallic, semi-conductor, glass, ceramic, or polymeric material. In some embodiments, the head 100 can have an applicator 114 with nanochips 140 shaped as a microknife, or microblade. In some embodiments, the nanochips 140 have a nanoscale tip or edge and a microscale body.

Aspect-ratio is defined as the ratio of the depth or height of a structure to its lateral dimension. High-aspect-ratio microstructures (HARMS) typically have an aspect ratio higher than about 5:1 and they may be useful for a variety of purposes. In the current application, the tip of nanochips 140 needs to be sharp in order to lower the insertion force, while the nanochips 140 should be high enough to allow it to completely penetrate stratum corneum.

A typical size of the needle tip is smaller than 10 microns, preferably smaller than 5 microns and the height of the microdevices is higher than 20 microns, preferably higher than 50 microns. The aspect ratio of these microdevices, in a preferred embodiment of the current invention, are higher than 10:1 with the size of the tip and edge smaller than 5 microns and the height of microdevices higher than 50 microns. HARMS can thus be used to fabricate microdevices including nanochips 140, microblades, and microknives for drug delivery through skin or body fluids extraction out of skin. Another example of HARMS is nanochannels for microfluidic manipulation and transport. HARMS is typically made by Micro-ElectroMechanical Systems (MEMS) and nanofabrication technology that involves a number of thin film deposition, photolithography, etching and electroplating, injection molding, hot embossing, self-assembly, as well as LIGA process.

The nanochips 140 can further include microchannels and microreservoirs. Some examples of the microdevice are described in U.S. application Ser. No. 10/908,584, filed on May 18, 2005 and Ser. No. 11/510,078, filed on Aug. 25, 2006. The teachings of both applications are incorporated herein in their entirety by reference.

In some embodiments, the nanochips 140 can also be used to collect body fluids, as opposed to delivering liquid or solid compositions. In this instance, the size of the nanochips 140 is bigger to enable efficient collection of the body fluids, as the nanochips 140 would need to reach the dermis layer of the skin of the patient.

The head 100 also comprises a housing 120. In one embodiment, the stem 110 passes through the housing 120. In another embodiment, the housing 120 extends beyond the second end 112 of the stem 110. In other embodiments, a part of the housing 120 that is proximate to the first end 111 of the stem 110 is provided with a second attachment means so that the head 100 securely attaches with the first end of the body 200 of the device 10.

In a preferred embodiment, the housing 120 holds the liquid or solid composition within it. In other embodiments, the housing 120 comprises a reservoir therein to hold the liquid or solid composition. The liquid or solid composition is sealed within the housing 120, or the reservoir, as the case may be, with the help of the applicator 114, and the sealant 116. In some embodiments, the liquid or solid composition is sealed within the housing 120, such that the stem 110 or the housing 120 needs to be twisted until the seal is broken so as to release the liquid or solid composition from the housing 120 or reservoir.

Further, in one embodiment, the head 100 comprises a mixing reservoir for storage and premixing or postmixing of the liquid or solid composition. In another embodiment, the housing 120 of the head 100 has an orifice for filling the liquid or solid composition. Further, in a preferred embodiment, the housing 120 additionally has a mixing chamber to mix a liquid composition with a solid composition or freeze drying solid composition during the axial movement of the stem 110 inside the housing 120.

In one embodiment, the housing 120 is made of polycarbonate or other suitable materials that are well known to a person of skill in the art.

The head 100 further comprises a flexible means 118. In one embodiment, the flexible means 118 is disposed on the stem 110. In another embodiment, the flexible means 118 is disposed between the stem 110 and housing 120. In a preferred embodiment, the flexible means 118 is a spring, although any object known to provide elasticity can be used.

In one embodiment, the flexible means 118 is used for providing movement of the stem 110 back and forth through the housing 120 to allow the applicator 114 to contact the patient's skin for delivery of the liquid or solid composition.

In a preferred embodiment, the stem 110 protrudes beyond the housing 120 when the flexible means 118, or spring, is in a compressed state, as shown in FIG. 3 of the present application. This is done to enable better contact of the applicator 114 with the patient's skin. Further, in another embodiment, the housing 120 provides a seal in conjunction with the attachment means at the second end 112 of the stem 110 thereby creating a vacuum when the stem 110 is in the up position (as shown in FIG. 2) such that the vacuum forces the composition in the housing 120 to be pulled through a seal between the attachment means at the second end 112 of the stem 110 and the housing 120, the composition, the applicator 114, and the housing 120 thereby contacting the patient's skin.

In some embodiment, a temporary pressure difference of the vacuum created by the axial movement of an end of the housing that contacts the patient's skin is less than 100000 Pa compared to ambient pressure.

In one embodiment, the sealant 116 around the applicator 114 helps create the vacuum within the housing 120, which further helps in drawing the liquid or solid composition onto the skin of the patient. In some embodiments, the selected dosage can be about between 0.001 ml/hr to 100 ml/hr.

Similarly, when an applicator 114 is used with nanochips 140 attached to the applicator 114, as shown in FIG. 3, the nanochips 140 create self-healing nanopores within the skin. Further, the vacuum created by the applicator 114 and the sealant 116 within the housing 120 helps in drawings the liquid or solid composition onto the skin of the patient, and through the nanopores that are created in the skin due to the nanochips 140.

The liquid or solid composition can be cosmetic agents which are used for dermal or transdermal delivery to a patient. In one embodiment, the cosmetic composition used is selected from a group consisting of hyaluronic acid and its derivatives, acetyl hexapeptide-3, vitamin A, vitamin C, vitamin E, alpha-hydroxyacids, and hormones. In another embodiment, the pharmaceutical composition is selected from a group consisting of antibiotics, hormones, steroids, anti-inflammatory drugs, protein drugs, drugs, recombinant Erythropoietin (rhEPO), Taxol®, Interferon-alpha-1b, Interferon beta, Interferon gamma, Emla®, Fluorouracil, Lidocaine, Salicylic acid, Pureriran, eflornithine hydrochloride, spironolactone, flutamide, insulin, nanoparticle drugs, Epidural, insulin, recombinant human parathyroid hormone, growth hormone, thyroid, cortisol, estrogen, progesterone, and testosterone and combinations thereof.

In other embodiments, the solid or liquid composition can be pharmaceutical agents which are active agents such as a natural or synthesized vaccine selected from the group consisting of vaccines, protein vaccines, peptide vaccines, gene vaccines and DNA vaccines against influenza (flu), diphtheria, tetanus, pertussis (DTaP), measles, mumps, rubella (MMR), hepatitis B, polio, haemophilus influenzae type b, chickenpox, tuberculosis, anthrax, yellow fever, rabies, AIDS, cancers, meningococcus, SARS and cholera. Additionally, in some embodiments, the pharmaceutical agents are diagnostic agents such as the group consisting of quantum dots, functionalized nanoparticles, magnetic particles or a combination of thereof.

In some embodiments, the patient is treated for medical conditions such as one or more cosmetic conditions selected from skin aging, skin wrinkle, dark spot, skin discoloration, moisturizing, skin lightening, skin whitening, skin firming, skin lifting, acne, wart, infection, irritation, dry skin and oily skin. Further, other embodiments treat the patient for AIDS, breast cancer, melanoma, liver cancer, lung cancer, blood cancer, pituitary tumors, other cancers, flu, infection, blood disease, cardiac disease, back pain, neck pain, body pain, general pain, arthritis, osteoporosis, headache, depression, smoke, alcoholic, overweight and obesity, menopause, facial hair growth, balding, polycystic ovary syndrome, need of inoculation, need of anesthetics and dermal diseases.

A method of delivery of the liquid or solid composition to the skin of a patient using the plunger-like mass transportation device, as described above. The method involves the steps of identifying an appropriate site on a skin of a patient; placing the device 10 such that the applicator 114 is placed proximately to the appropriate site on the skin of the patient; activating the device 10; and delivering the liquid or solid composition via the applicator 114 on the skin of the patient.

In one embodiment, the method further comprises the step of creating nanopores within the skin of the patient for transdermal delivery of the liquid or solid composition. In another embodiment, an occlusive layer is placed over the skin, after treatment with the plunger-like mass transportation device 10 for an extended release of the liquid or solid composition. In some embodiments, a liquid composition is pumped using a pump to the occlusive layer for infusion of the composition through the patient's skin. In certain embodiments, the infusion rate to the occlusive layer is greater than 0.001 ml/hr.

As an exemplary experiment to demonstrate the creation of self-healed nanopores using the plunger-like mass transportation device, a balloon was partially filled with water, and the device 10 was used with a head 100 having an applicator 114 with nanochips was used on the surface of the water-filled balloon. As the device was used on the balloon, water started seeping through the nanopores that were created on the surface of the balloon, which has a thickness of more than 10 microns. It is important to point out that the integrity of the balloon was kept during and after this treatment. Furthermore, water stopped seeping through the nanopores if the air in the balloon was released for more than 10 second, indicating the nanopores self-healed because the elasticity of the balloon. This experiment indicates how using the device on the skin of a patient can create self-healed nanopores.

With the information contained herein, various departures from precise descriptions of the present subject matter will be readily apparent to those skilled in the art to which the present subject matter pertains, without departing from the spirit and scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter, which are obvious to those skilled in chemistry, or biochemistry, or related fields are intended to be within the scope of the following claims.

I claim:

1. A mass transporting device for controllable transportation of a selected dosage of a solid or liquid composition comprising:
   a body having a rigid enclosure, and
   a head, the head configured to attach to the body, the head having a stem and a housing, the stem having:
   a first end; and
   a second end; wherein a flexible means is disposed on the stem, for providing an up position and a down position during an axial movement of the stem back and forth through the housing, wherein the housing contains the solid or liquid composition, wherein nanochips with solid structures are attached to an applicator at the second end of the stem to facilitate the mass transportation;
   wherein the housing provides a seal in conjunction with a flexible seal at the second end of the stem, thereby creating a vacuum when the stem is in the up position such that the vacuum forces the composition in the housing to be pulled through the flexible seal, the composition and the housing thereby configured to contact a patient's skin.

2. The device of claim 1, wherein the flexible means is a spring.

3. The device of claim 1, wherein the housing extends beyond the second end of the stem.

4. The device of claim 1, wherein the stem protrudes beyond the housing when the flexible means is in a compressed state.

5. The device of claim 1, wherein said flexible seal is a sealed ring.

6. The device of claim 1, wherein the head is removable.

7. The device of claim 1, wherein the head is configured to hold 0.01-30 ml of cosmetic or pharmaceutical composition.

8. The device of claim 1, wherein the nanochips are made of silicon.

9. The device of claim 1, wherein the device is configured to provide an up-down axial movement to the stem.

10. The device of claim 1, wherein the liquid or solid composition is selected from a group consisting of EGF, collagen, insulin, lidocaine, and botox.

11. The device of claim 1, wherein an attachment means is present on the housing, to attach the head to the body.

12. A method of delivery of a cosmetic or pharmaceutical composition to a skin of a patient using the device of claim 1 comprising:
   identifying an appropriate site on the skin of the patient;
   placing the device such that the applicator is placed proximately to the appropriate site on the skin of the patient;
   activating the device; and
   delivering the liquid or solid composition through the applicator on the skin of the patient.

13. The method of claim 12, further comprising creating nanopores on a portion of the skin of the patient for transdermal delivery of a cosmetic or pharmaceutical composition.

14. The method of claim 12, further comprising placing an occlusive layer over the appropriate site on the skin of the patient.

15. The method of claim 14, further comprising pumping the liquid composition using a pump to the occlusive layer for infusion of the composition through the patient's skin.

* * * * *